United States Patent
Guo

(10) Patent No.: US 10,251,687 B2
(45) Date of Patent: Apr. 9, 2019

(54) DEVICE AND METHOD FOR FIXING ACETABULAR FRACTURES INVOLVING THE ANTERIOR/POSTERIOR COLUMN AND QUADRILATERAL PLATE

(71) Applicant: Xiaodong Guo, Hubei (CN)

(72) Inventor: Xiaodong Guo, Hubei (CN)

( * ) Notice: Subject to any disclaimer, the term of this patent is extended or adjusted under 35 U.S.C. 154(b) by 0 days.

(21) Appl. No.: 15/661,006

(22) Filed: Jul. 27, 2017

(65) Prior Publication Data

US 2017/0319249 A1    Nov. 9, 2017

Related U.S. Application Data

(63) Continuation of application No. PCT/CN2016/073179, filed on Feb. 2, 2016.

(30) Foreign Application Priority Data

| Feb. 5, 2015 | (CN) | 2015 1 0060741 |
| Feb. 5, 2015 | (CN) | 2015 1 0061823 |
| Feb. 5, 2015 | (CN) | 2015 2 0082407 U |
| Feb. 5, 2015 | (CN) | 2015 2 0083227 U |
| Sep. 1, 2015 | (CN) | 2015 1 0555387 |
| Sep. 1, 2015 | (CN) | 2015 2 0674722 U |
| Sep. 1, 2015 | (CN) | 2015 2 0680145 U |
| Sep. 1, 2015 | (CN) | 2015 2 0680781 U |

(51) Int. Cl.
*A61B 17/80* (2006.01)
*A61B 17/84* (2006.01)
*A61B 17/86* (2006.01)

(52) U.S. Cl.
CPC .......... *A61B 17/8066* (2013.01); *A61B 17/80* (2013.01); *A61B 17/8023* (2013.01); *A61B 17/8052* (2013.01); *A61B 17/8085* (2013.01); *A61B 17/848* (2013.01); *A61B 17/86* (2013.01)

(58) Field of Classification Search
CPC . A61B 17/8066; A61B 17/80; A61B 17/8023; A61B 17/8052; A61B 17/8085
See application file for complete search history.

(56) References Cited

FOREIGN PATENT DOCUMENTS

CN          201831946 U     5/2011

*Primary Examiner* — Christian Sevilla

(57) ABSTRACT

Disclosed are a device for fixing acetabular fractures involving the anterior/posterior column and acetabulum quadrilateral plate and a usage method thereof. The device includes an iliopectineal plate and an trapezoidal plate or a pubic plate. The iliopectineal plate and the pubic plate are integrally bent to match with a medial anatomic structure of an iliopectineal line and a superior pubic ramus. The shape of trapezoidal plate matches with the acetabular quadrilateral plate, the anterior column and the posterior column to fix the posterior column, an ischium and the acetabulum quadrilateral plate from inside to outside. The device is at the medial surface of the iliopectineal line, which fixes the fragments of the acetabulum quadrilateral plate in an opposite direction and fixes the acetabular fracture stably for improving the quality of reduction and fixation.

13 Claims, 5 Drawing Sheets

DEVICE AND METHOD FOR FIXING ACETABULAR FRACTURES INVOLVING THE ANTERIOR/POSTERIOR COLUMN AND QUADRILATERAL PLATE

CROSS-REFERENCE TO RELATED APPLICATION

This application is a continuation application of PCT Application No. PCT/CN2016/073179 filed on Feb. 2, 2016, which claims priority to Chinese Application No. 201510060741.3 filed on Feb. 5, 2015, Chinese Application No. 201510061823.X filed on Feb. 5, 2015, Chinese Application No. 201520082407.3 filed on Feb. 5, 2015, Chinese Application No. 201520083227.7 filed on Feb. 5, 2015, Chinese Application No. 201510555387.1 filed on Sep. 1, 2015, Chinese Application No. 201520674722.5 filed on Sep. 1, 2015, Chinese Application No. 201520680145.0 filed on Sep. 1, 2015, and Chinese Application No. 201520680781.3 filed on Sep. 1, 2015. The entire contents of all the above are hereby incorporated by reference.

TECHNICAL FIELD

This new device relates to the field of medical apparatus and instruments of the department of orthopaedics. More specifically, it's a fixation device for the anterior and posterior column fracture of the acetabulum, in particular for the quadrilateral plate fracture.

BACKGROUND

Comminuted acetabular fractures have always been a difficult problem in the department of traumatic orthopaedics. The complex structures of vascular and nervous around the operative area create difficulty in the acetabular fracture reduction, as well as the inability of exposure and the limited area for the screw insertion. Complex acetabular fractures, which are comminuted fractures of the anterior column or posterior column or even both columns can occur at the same time due to sever trauma, are often combined with an acetabulum quadrilateral plate fracture. For the surgical treatment of this kind of fractures, it is prone to hip osteoarthritis, necrosis of the femoral head and so on because of poor fracture reduction.

At present, the surgical treatment of acetabular fractures involving the quadrilateral plate mainly includes the fixation of the anterior column using plates after reduction of the fracture by an anterior approach, and then using lag screws to fix the posterior column or adding another posterior approach.

At present, there are many problems in the surgical treatment of acetabular fracture such as difficulty of fracture reduction, difficulty of shaping and placing plate after reduction, instable fixation, high risk of damaging the blood vessels and nerves, long operative time, large amount of bleeding and many postoperative complications et. al. In addition, the current surgical method is difficult to fix the quadrilateral plate fracture especially when the fractures are severely comminuted and displaced. It may result in big surgical trauma, unsatisfactory fracture reduction and fixation, malunion of fracture, postoperative traumatic arthritis, femoral head necrosis and other bad outcome. For some osteoporotic patients, it is more likely that occurring loosening or displacement of the internal fixations. How can we effectively deal with this type of fracture is the focus of current research.

The patent CN201831946U discloses an anatomical plate of the acetabulum quadrilateral plate that includes a long strip of plate and a buttress plate fixing the fracture of the quadrilateral area. But there are some disadvantages: the mechanical mismatch with the displacing direction of fracture, the limited fixation of quadrilateral plate, and the problem that the anterior and posterior columns can't be fixed simultaneously. Consequently, better internal fixation devices need be invented as soon as possible.

SUMMARY

An object of the invention is to provide a novel fixation device of acetabular anterior/posterior column involving quadrilateral area which could overcome the deficiency mentioned in background technique. The fixation device can fix the fracture more accurately and effectively. The using methods of the fixation device for ensuring the convenience of the application and the reliability of the fixation are also provided.

In order to achieve the above purpose, the fixation device comprises an iliopectineal plate and a pubic plate. The iliopectineal plate matches with a medial anatomic structure of an iliopectineal line. One end of the iliopectineal plate is designed with a first screw hole matching the iliopectineal line near a superior pubic ramus and the other end of the iliopectineal plate is designed with a posterior column arm matching the iliopectineal line near an iliac fossa. A groove is disposed at an adjacent of the iliopectineal plate and the first screw hole. The posterior column arm laterally extends from the iliopectineal plate and matches with an anatomic structure that from the iliopectineal line to the iliac fossa, the posterior column arm is disposed with at least one screw hole.

The posterior column arm laterally extends from the iliopectineal plate, matching with the anatomic structure that from the iliopectineal line to the iliac fossa. The posterior column arm is disposed with at least one screw hole. The pubic plate is disposed transversely in an arcuate way and is bent to fit a medial anatomic structure of the superior pubic ramus. One end of the pubic plate is designed with a second screw hole that matches with the superior pubic ramus near a pubic symphysis and the other end of the pubic plate is designed with a pubic arm extending to an upper surface of a pecten pubis near a pubic tubercle. The second screw hole is thinned into a step at an adjacent end of an arcuate plate. The iliopectineal plate and the pubic plate are provided with at least one Kirschner wire temporary fixing hole. The groove of the first screw hole of the iliopectineal plate and the thinned step of the second screw hole of the pubic plate match with each other. The first screw hole and the second screw hole are implemented with screws after being aligned. The iliopectineal plate and the pubic plate are combined into a whole. The whole matches with anatomical structures of inner sides of the superior pubic ramus, an acetabulum quadrilateral plate and a posterior column.

In the above technical solution, the pubic arm is designed with at least one combined screw. The pubic arm is provided with at least one combined screw. The posterior column arm is provided with at least two combined screw holes and fixed by long lag screws or long locking screws. The screw holes of the iliopectineal plate and the pubic plate are in a form of combined screw holes.

A method of using a device for fixing acetabular fractures involving the anterior/posterior column and quadrilateral plate, the method comprising:

a) placing and connecting plates
matching an iliopectineal plate and an pubic plate with an inner anatomic structure of an iliopectineal line, an acetabulum quadrilateral plate and a superior pubic ramus by taking the iliopectineal line and the superior pubic ramus as a reference point; and inserting a short connecting screw into a first screw hole of the iliopectineal plate and a second screw hole of the pubic plate to make the iliopectineal plate and the pubic plate integrate together after the first screw hole of the iliopectineal plate and the second screw hole of the pubic plate are aligned;
b) temporarily fixing the plates
choosing two or three Kirschner wire temporary fixing holes on the iliopectineal plate, the pubic plate and a posterior column arm to be inserted with a kirschner wire respectively; and temporarily fixing the iliopectineal plate, the pubic plate and the posterior column arm on an anatomical structure;
c) fixing the anterior column and the acetabulum quadrilateral plate
inserting a screw into the iliopectineal plate and the pubic plate respectively for attaching the plate to a bone surface and also for fixing an upper part of the anterior column and the acetabulum quadrilateral plate;
d) fixing the posterior column
selecting two screw holes of the posterior column arm to be inserted with a long locking screw to fix the posterior column; and firstly inserting a long lag screw to further reduce the fracture well due to a small gap between the posterior column plate and the bone surface, and then inserting a locking screw;
e) fixing other screws
fixing the iliopectineal plate and the pubic plate firmly by inserting screws into rest appropriate screw holes; and in view of a longitudinal cleft fracture of a pubis, using a third screw hole on an arm of a pubic arm to fix the superior pubic ramus in a way perpendicular to a fracture line; and in view of no longitudinal cleft fracture of the pubis, broking off the pubic arm from the pubic plate.

A device for fixing acetabular fractures involving the anterior/posterior column and quadrilateral plate comprises a trapezoidal plate and a pubic plate.

An upper part of the trapezoidal plate is a transversely arranged iliopectineal plate. The iliopectineal plate bends to match an anatomic structure of a medial side of an iliopectineal line. One end of the iliopectineal plate is matched with the iliopectineal line near an superior pubic ramus where a first screw hole is provided. A transversely arranged groove is provided from the iliopectineal plate to an adjacent end of the first screw hole.

The other end of the iliopectineal plate is provided with a longitudinal arranged posterior column plate. The posterior column plate constitutes one side of the trapezoidal plate. The posterior column plate bends to fit an anatomic structure of a medial side of the posterior column. The top of the posterior column plate connects to one end of the iliopectineal plate and bends toward an iliac fossa to extend from a posterior column arm. The posterior column arm matches with an anatomic structures of the iliac fossa and the iliopectineal line.

The bottom of the posterior column plate is attached to a sciatic plate. The sciatic plate is transversely disposed in the lower part of the trapezoidal plate. The sciatic plate bends to fit an anatomic structure of a medial side of an ischium.

The posterior column arm, the posterior column plate and the sciatic plate are provided with at least one screw hole and at least one Kirschner wire temporary fixing hole.

An area between the sciatic plate and the iliopectineal plate is a quadrilateral buttress plate with a thin palisade structure 23. The area matches with the anatomic structure of an acetabulum quadrilateral plate, a posterior column window and a quadrilateral plate window are designed on the quadrilateral buttress plate.

The pubic plate is curved and bent to match with an anatomic structure of the superior pubic ramus. A second screw hole is disposed on the place where an end of the pubic plate is matched with the superior pubic ramus near a pubic symphysis. A portion from the second screw hole to an adjacent end of the pubic plate is thinned to a step.

A groove of the first screw hole on the iliopectineal plate is matched with the thinned step of the second screw hole on the pubic plate. A screw is inserted into the first screw hole and the second screw hole for fixing after the first screw hole and the second screw hole are aligned. The trapezoidal plate and the pubic plate are combined as a whole and the whole matches with the anatomical structures of the acetabulum quadrilateral plate and the medial surface of the pubic ramus and the ischum.

In the above technical solution, at least one combined screw hole is provided on the pubic arm.

A vacancy area between the quadrilateral buttress plate and the posterior column plate is a posterior column window. The posterior column window is located on the upper front part of the posterior column.

At least two combined screw holes are disposed on the posterior column arm and fixed with a long lag screw or a long locking screw. At least three combined screw holes are disposed on the posterior column plate and the sciatic plate. All the screw holes disposed in the iliopectineal plate and the pubic plate are combined holes.

A method of using a device for fixing acetabular fractures involving the anterior/posterior column and quadrilateral plate, the method comprising:
a) placing and connecting plates
matching a trapezoidal plate and a pubic plate with an anatomical surface of an iliopectineal line and an acetabulum quadrilateral plate by taking the iliopectineal line, a superior pubic ramus and the acetabulum quadrilateral plate as a reference point; and inserting a short connecting screw into a first screw hole of the trapezoidal plate and a second screw hole of the pubic plates to make the trapezoidal plate and the pubic plate connected as a whole after the first screw hole of the trapezoidal plate and the second screw hole of the pubic plates are aligned;
b) temporarily fixing the plates
selecting two or three Kirschner wire temporary fixing holes to temporarily fix the trapezoidal plate and the pubic plate on an anatomical structure; and applying a fluoroscopy to observe a reduction of the fracture;
c) fixing an anterior column
inserting a screw into the iliopectineal plate and the pubic plate respectively for fixing the iliopectineal plate and the pubic plate on the anterior column;
d) fixing the posterior column
if the posterior column and the acetabulum quadrilateral plate have a good restoration, selecting one screw hole of a posterior column plate or a sciatic plate to be inserted with a screw for attaching the posterior column plate or the sciatic plate to a bone surface of the acetabulum quadrilateral plate and also fixing the posterior column and the acetabulum quadrilateral plate;
if the posterior column and the acetabulum quadrilateral plate do not have a good restoration but have some micro displacement, inserting a ball-spike pusher or a pulling hook into a posterior column window or a quadrilateral plate window for operation; and further applying an anatomical reduction on the micro displacement; then inserting a screw into at least one the screw hole of the posterior column plate or the posterior column to fix the posterior column and the acetabulum quadrilateral plate;

e) fixing other screws fixing the trapezoidal plate and the pubic plate firmly by inserting screws into the rest appropriate screw holes.

A device for fixing acetabular fractures involving the anterior/posterior column and quadrilateral plate comprises a strip-like iliopectineal plate and a trapezoidal plate.

The iliopectineal plate is set as a transverse strip and the back side of the iliopectineal plate is bent to fit an anatomic structure of an iliopectineal line.

Both ends of the iliopectineal plate are respectively provided with at least one ilium fixing hole and at least one pubis fixing hole. At least one iliopectineal line fixing hole is provided in the middle of the iliopectineal plate. The ilium fixing hole is set near an iliac fossa, the pubis fixing hole is set on a superior pubic ramus.

The trapezoidal plate is transversely disposed on a lower part of the iliopectineal plate and is bent to match with an inner side anatomic structure of an upper part of an ischium and an upper part of an acetabulum quadrilateral plate. An upper part of the trapezoidal plate is matched with a bone surface anatomic structure from a greater sciatic notch to an obturator foramen transversely. A posterior column plate, a posterior column window and a quadrilateral buttress plate are disposed on the upper part of the trapezoidal plate in turn. The top of the posterior column plate is located below the ilium fixing hole and extends toward an ischial spine along a bone surface of a posterior column. The quadrilateral buttress plate is located on the acetabulum quadrilateral plate.

At least one posterior column fixing hole is provided on the posterior column plate. A quadrilateral plate window is provided on the quadrilateral buttress plate.

A sciatic plate is also arranged transversely at the bottom of the trapezoidal plate. The sciatic plate is located at the bottom of the posterior column plate and is below the posterior column window and the quadrilateral buttress plate. The sciatic plate is curved to fit the anatomic structure of the inside of the ischium. The sciatic plate is provided with an ischial fixing hole.

When the iliopectineal plate and the trapezoidal plate are attached to an inner surface of the iliopectineal line and an upper surface of the posterior column or an anterior column, the bottom of the sciatic plate of the trapezoidal plate is located at the bottom of the ischial spine and the top of the lesser sciatic notch. Alternatively, the bottom of the sciatic plate of the trapezoidal plate is disposed at the position from the middle of the greater sciatic notch and the ischial spine to the bottom of the obturator foramennear the acetabulum quadrilateral plate.

In the above technical solution, the pubis fixing hole and the ilium fixing hole on the iliopectineal plate are universal locking screw holes which inserted with locking screws.

The trapezoidal plate is provided with at least two posterior column fixing holes and each posterior column fixing hole is a universal locking screw hole which is inserted with a locking screw.

The sciatic plate is provided with at least two sciatic fixing holes and each sciatic fixing holes is a universal locking screw which is inserted with a locking screw.

At least one Kirschner wire temporary fixing hole is arranged at each end of the iliopectineal plate. At least one Kirschner wire temporary fixing hole is provided on the bottom and the top of the trapezoidal plate.

A device for fixing acetabular fractures involving the anterior/posterior column and quadrilateral plate comprises a strip-like iliopectineal plate and a trapezoidal plate combined with the strip-like iliopectineal plate as a whole.

The iliopectineal plate is arranged stripe-likely in a transverse direction and is curved to fit an anatomy of an inner side of an iliopectineal line. Both ends of the iliopectineal plate are provided with at least one ilium fixing hole and at least one pubis fixing hole. The ilium fixing hole is near a fossa iliaca, the pubis fixing hole is located on a superior pubic ramus.

At least three fixing arms are provided between the top middle of the trapezoidal plate and the bottom middle of the iliopectineal plate. The bottom of each fixing arm is set at the top of the trapezoidal plate or the bottom of the iliopectineal plate. The top of each fixing arm is provided with an arm fixing hole. The bottom of the iliopectineal plate or the trapezoidal plate which is not provided with the fixing arms is provided with an arm fixing and mounting hole.

A distal end of the fixing arm is provided with a thin step-like fixing arm hole. Each arm fixing and mounting hole is a sinking two-layer step round hole. Each fixing arm hole and the corresponding arm fixing and mounting hole are matched with each other. The fixing arm hole and the corresponding arm fixing and mounting hole are inserted by a screw to combine the trapezoidal plate and iliopectineal plate as a whole. The whole matches with the anatomic structure of the anterior column and the iliopectineal line.

The trapezoidal plate is arranged transversely in the lower part of the iliopectineal plate and curved with an anatomic structure of the ischium and the upper half of the acetabulum quadrilateral plate. The upper part of the trapezoidal plate is matched with the anatomic structure of a greater sciatic notch transverse to an obturator foramen, and a posterior column plate, a posterior column window and a quadrilateral buttress plate are disposed on the upper part of the trapezoidal plate in turn. When the iliopectineal plate and the trapezoidal plate are integrated, the top of the posterior column plate is located below the ilium fixing hole and extends along a posterior column to an ischial spine. The quadrilateral buttress plate is located on the acetabulum quadrilateral plate.

The posterior column plate is provided with at least one posterior column fixing hole. An quadrilateral plate window is disposed on the acetabular quadrilateral buttress plate.

A transverse part is set on the lower part of the trapezoidal plate which is integrally bent to match with the upper part of the ischium and the inner upper part of the acetabulum quadrilateral plate and also match with the bone surface anatomic structure from the greater sciatic notch to the obturator foramen.

In the above technical solution, the posterior column plate, the posterior column window and the acetabular quadrilateral buttress plate are disposed on the trapezoidal plate in turn. At least one posterior column fixing hole is provided on the posterior column plate. The quadrilateral plate window is provided on the acetabular quadrilateral buttress plate.

When the iliopectineal plate and the trapezoidal plate are integrally attached to the inner side of the iliopectineal line and the upper surface of the anterior column, the top of the posterior column plate locates below the ilium fixing hole and extends to the ischial spine along the posterior column. The bottom of the posterior column plate is located in the middle part from the greater sciatic notch to the ischial spine. The acetabular quadrilateral buttress plate is located on the upper part of the acetabulum quadrilateral plate. The bottom of the acetabular quadrilateral buttress plate has an equal height with the outer bottom of the obturator foramen near the acetabulum quadrilateral plate.

In the above technical solution, the posterior column plate, the posterior column plate window and the acetabular quadrilateral buttress plate are disposed on the upper part of the trapezoidal plate in turn. The sciatic plate is arranged on the bottom of the trapezoidal plate. The posterior column plate is provided with at least one posterior column fixing hole. The quadrilateral plate window is provided on the acetabular quadrilateral buttress plate. The sciatic plate is provided with at least one ischium fixing hole.

When the iliopectineal plate and the trapezoidal plate are integrally attached to the upper surface of the iliopectineal line and the upper surface of the anterior column, the top of the posterior column is located below the ilium fixing hole and extends to the ischial spine along the posterior column. The sciatic plate is located transversely at the bottom of the ischial spine and at the top of the lesser sciatic notch. The acetabular quadrilateral buttress plate is located on the upper part of the acetabulum quadrilateral plate. The bottom of the acetabular quadrilateral buttress plate has an equal height with the bottom of outer edge of the obturator foramen near the acetabulum quadrilateral plate.

In the above technical solution, all the arm fixing hole and the arm fixing and mounting hole are combined screw holes, which could be inserted with ordinary screws or combined screws.

The pubis fixing hole and the ilium fixing hole on the iliopectineal plate are universal locking screw holes inserted with locking screws. The trapezoidal plate is provided with at least two posterior column fixing holes. Each posterior column fixing hole is a universal locking screw hole inserted with the locking screw.

The sciatic plate is provided with at least two sciatic fixing holes. Each sciatic fixing hole is a universal locking screw hole which inserted by a locking screw.

Each end of the iliopectineal plate is provided with at least one Kirschner wire temporary fixing hole. At least one Kirschner wire temporary fixing hole is arranged at the bottom and the top of the trapezoidal plate.

A method of using a device for fixing acetabular fractures involving the anterior/posterior column and quadrilateral plate, the method comprising:

a) placing and connecting plates matching an iliopectineal plate and a trapezoidal plate with an anatomic structure of an iliopectineal line and an acetabulum quadrilateral plate by taking the iliopectineal line, a superior pubis ramus and the acetabulum quadrilateral plate as reference points; and inserting a connection screw into every arm fixing hole and every corresponding arm fixing and mounting hole on the trapezoidal plate and the iliopectineal plate to make the iliopectineal plate and the trapezoidal plate connected as a whole after the arm fixing hole and the arm fixing and mounting hole are aligned;

b) temporarily fixing the plates selecting one or two Kirschner wire temporary fixing holes of the iliopectineal plate and the trapezoidal plate respectively and temporarily fixing the iliopectineal plate and the trapezoidal plate on an anatomic structure; and observing a reduction of the fracture through a quadrilateral plate window and a posterior column window;

c) fixing the iliopectineal line inserting a screw into at least one pubis fixing hole and at least one ilium fixing hole on the iliopectineal plate respectively for fixing the iliopectineal plate on the iliopectineal line;

d) fixing the posterior column if the posterior column and the acetabulum quadrilateral plate are restored well, one posterior column fixing hole on a posterior column plate or one sciatic fixing hole on a sciatic plate is inserted with one screw to make the posterior column plate or the sciatic plate be attached to the bone surface of the acetabular quadrilateral plate and fix the posterior column and the acetabulum quadrilateral plate;

if the posterior column and the acetabulum quadrilateral plate do not have a good restoration but have some micro displacement, inserting a ball-spike pusher and a pulling hook into a quadrilateral plate window of a quadrilateral buttress plate for operation; and further applying an anatomical reduction on the micro displacement; then inserting a screw into at least one posterior column fixing hole or at least one sciatic fixing hole to fix the posterior column and the acetabulam quadrilateral plate;

e) Inserting the remaining screws fixing the iliopectineal plate and the trapezoidal plate firmly by inserting screws into the rest appropriate screw holes.

Figure 1:
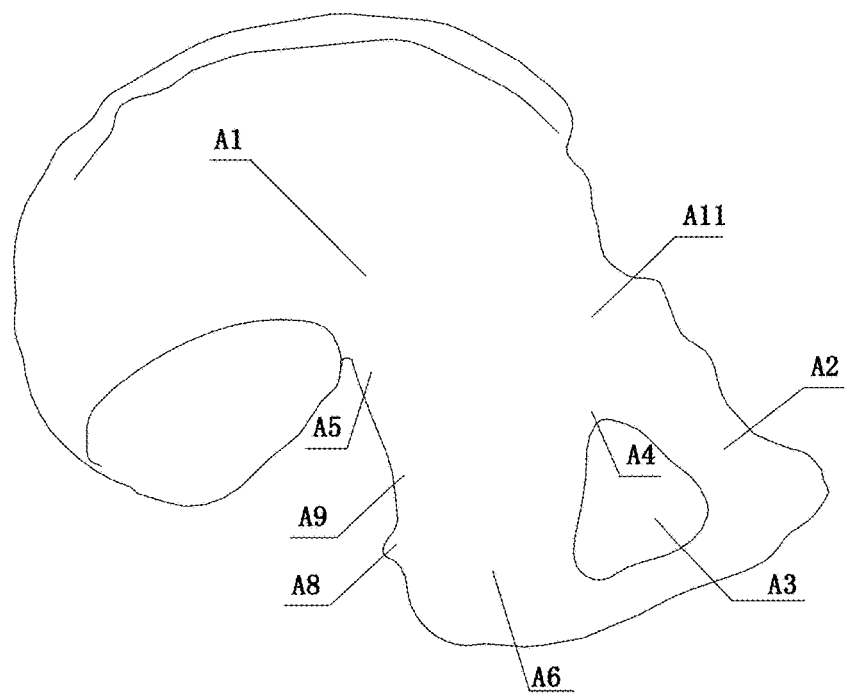
FIG. 1 is a sketch of the acetabular and its adjacent anatomic structures.

In the figures: iliac fossa A1, superior pubic ramus A2, obturator foramen A3, quadrilateral plate A4, iliopectineal margin A5, ischium A6, lesser sciatic notch A7, ischial spine A8, posterior column A9, greater sciatic notch A10, anterior column A11; Extending fixation arm C.1, hole of fixing arm C.2, hole for fixing and mounting the fixing arm C.3; first screw hole D1, second screw hole D2, third screw hole G; Iliopectineal plate B1, pubic plate B2, posterior column arm B3 (middle fixing hole of the iliopectineal margin B3.1 pubis fixing hole B3.2 ilium fixing hole B3.3), pubic arm B4, trapezoidal plate B5, posterior column plate 4 (posterior column fixing hole 4.1), quadrilateral buttress plate 5, posterior column window 8, acetabulum quadrilateral plate 9, sciatic plate 10 (sciatic fixing hole 10.1), temporary fixing hole of Kirschner wire 12, groove 21, step 22.

DETAILED DESCRIPTION OF THE EMBODIMENTS

The implementation of the invention is described in detail with combinations of these drawings, but it is only listed as an example so does not constitute a limitation on the invention. The invention is further described in detail by the specific implementation.

The sketch of the acetabular and its adjacent anatomic structures are shown in FIG. 1. The acetabulum is composed of the pubis, the ischium and the ilium. The acetabulum is enclosed by the anterior column A11 and the posterior column A9 like the two limbs of an inverted Y. The anterior column A11 is located at the anterior side of the acetabulum, and the lower half part of the anterior column A11 includes iliopectineal eminence and an superior pubic ramus A2. The posterior column A9 is located at the posterior side of the acetabulum, mainly comprising by the ischium A6, the ischial spine A8, the posterior half part of the acetabulum, and the compact bone forming the greater sciatic notch.

The two sides of the ischial spine A8 are greater sciatic notch A10 and lesser sciatic notch A7. The anterior column A11 and the posterior column A9 embrace the acetabulum just like a cradle and meet in the medial side of the acetabulum, which forms the medial wall of the acetabulum and the outer wall of the true pelvis. The upper part of the hip bone is the iliac fossa A1. The lower boundary of the iliac fossa A1 is iliopectineal margin A5, which is an smooth bone crest locating at lower inner surface of the iliopectineal line. The iliopectineal margin A5 is part of the lateral wall of the true pelvis. The obturator foramen is below the hip bone A3. The purpose of acetabular surgery or nonoperative treatment is to restore the concentric structures of the acetabulum and the femoral head.

Embodiment 1

Figure 2:
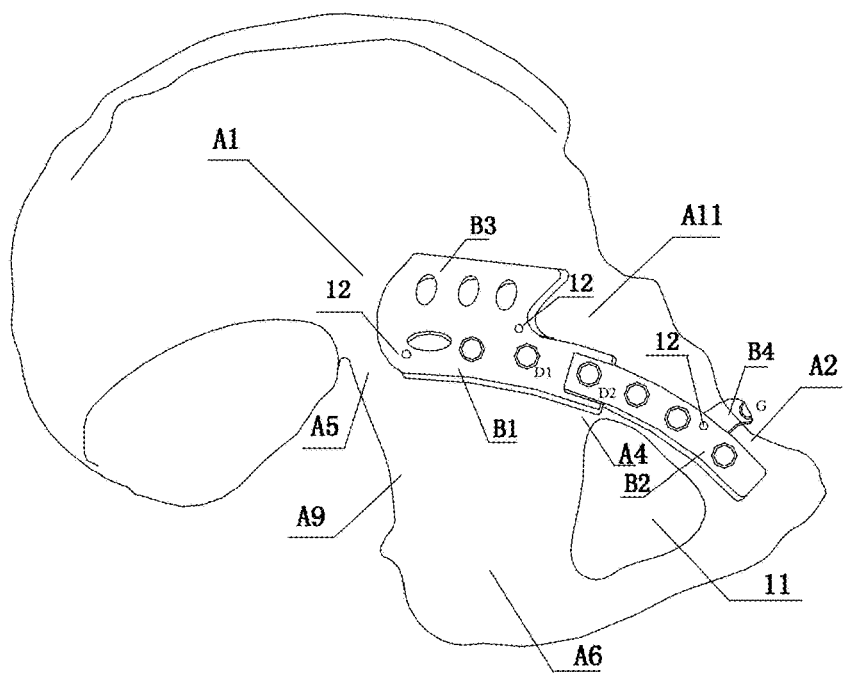
FIG. 2 is a schematic diagram of the embodiment 1 that a device for fixing the acetabular anterior/posterior column and quadrilateral plate fracture, which has been installed on the acetabulum.
Figure 3:
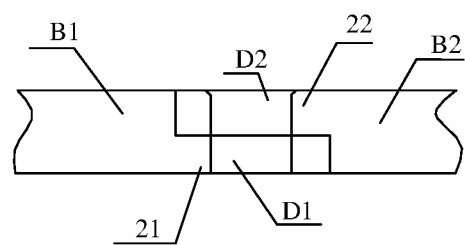
FIG. 3 is a sectional plan of the first screw hole and the second screw hole.

As shown in FIGS. 2 and 3, the device for fixing acetabular anterior and posterior column fracture includes: iliopectineal plate B1 and pubic plate B2. Both plates are in the same thickness and made of medical stainless steel or titanium alloy.

Iliopectineal plate B1 is an equally wide curved plate, which bents fitting to the medial anatomic physiological radian of the iliopectineal margin A5. One end of the iliopectineal plate B1 is located near the superior pubic ramus A2 with the first screw hole D1 (the connecting screw hole). The other end is located close to the iliac fossa A1 with the posterior column arm B3. Iliopectineal plate B1 has several combined screw holes from the outside to the inside of the iliopectineal margin, which can be inserted into ordinary screws or locking screws; Designed in the central of outer and upper edge of the iliopectineal plate B1 are respectively a temporary Kirschner wire fixation hole 12.

The arm of the posterior column B3 bends together with the anatomic physiologic radian of the upper edge of the iliopectineal margin A5 to the iliac fossa A1. The upper side of the column is designed with several combined holes from the outside to the inside, which has guiding function so that the long lag screw or long locking screw can be safely placed into the posterior column A9 to fix the higher or lower fracture of the posterior column A9.

The pubic plate B2 is an equally wide curved plate which is bent to match the medial anatomic structure of the superior pubic ramus A2 and fixed to the medial margin of superior pubic ramus A2. One end of the pubic plate B2 is designed with the first hole D2 (connecting screw hole) near the pubic syphysis. The other end is designed with the pubic arm B4 extending to the surface of pubic pecten near the pubic tubercle.

Several combined screw holes are designed on the pubic plate B2, which can be inserted into ordinary screws or a locking screw. The pubic arm B4 and pubic plate B2 is aligned with the superior surface of the superior pubic ramus A2. The third screw hole G on pubic arm B4 is a combined screw fixed on the surface in the superior pubic ramus A2 using ordinary screws or locking screws for the fixation of pubic longitudinal displaced fracture. One temporary fixing hole of Kirschner wire 12 is designed on the upper middle part of the pubic plate B2.

The junction between pubic arm B4 of the pubic plate B2 is breakable. When there is transverse fracture of pubic bone, there is no need to fix the pubic arm B4, thus, so the pubic arm can be broken and removed directly during operation. When there is longitudinal fracture of pubic bone, the pubic arm B4 is fixed through the third screw hole G to fix the longitudinal fracture from top to bottom perpendicularly.

The first hole D1 of the iliopectineal plate B1 is designed with a groove 21 of half of the integral plate thickness. The second screw hole D2 of pubic plate B2 is also designed with half of the overall thickness, forming a step 22. When the iliopectineal plate B1 and the pubic plate B2 are assembled together, the shape of the groove 21 at the first screw hole D1 is in perfect conformity with the shape of the stair 22 at the second hole D2. After the step 22 of the second screw hole D2 matches well with the groove 21 of the first screw hole D1, a short connective screw is used to cross the two holes to fix the iliopectineal plate B1 and the pubic plate B2 into the pubic body as a whole. The combination of the iliopectineal plate B1 and the pubic plate B2 does not move or rotate with each other, nor does it move or rotate on the anatomical position.

The fixing device for the fixation of anterior column A11 and posterior column A9 fractures of the acetabulum is mounted on the hip bone; the shape of the pubic plate B2 and the iliopectineal plate B1 is consistent with the quadrilateral surface A4 as well as the anterior column A11 and posterior column A9, especially the medial surface of superior pubic ramus A2 and iliopectineal margin A5. The plate need not be bent during operation result in an easier operative procedure.

Referring to the anatomic physiological radian between the inner side of the ilio-pectineal margin A5 and the iliac fossa A5, the ilio-pectineal plate B1 is localized to the medial surface of ilio-pectineal margin A5. With reference to the physiological radian of the superior pubic ramus A2, the pubic plate B2 was positioned on the medial surface of the superior pubic ramus A2. The step 22 at the second hole D2 of the pubic plate B2 is able to be matched with the groove 21 at the first hole D1 of the ilio-pectineal plate B1, then a short connecting screw can be inserted into the holes combining the two plates into a whole. As holes between the first hole D1 of the ilio-pectineal plate B1 and the second hole D2 of the pubic plate B2 is located near the joint area, none screw will be inserted generally. If necessary we can also use shorter screws to avoid implanting into the hip joint cavity.

In the field of creating new medical devices, especially the design and application of anatomical plate, there are three commonly types of screw holes as follow: ordinary screw holes, locking screw holes and combined screw holes. The common screw holes are suitable for ordinary screws, and the screw holes and the nuts of the common screws are free of thread; the concrete is as follows: cancellous screws, cortical screws and lag screws etc. The locking screw hole is suitable for the locking screw. When the oblique screw hole in the device is used, a screw thread with guiding function is arranged in the locking screw hole, and the correspondent screw nuts is also designed with a screw thread. The guiding role of the locking screw hole make the screw inserted into the specified location, then screw and plate are connected by the locking screws, so it is not easy to loosen. The combined screw hole is composed of an ordinary screw hole and a locking screw hole, and it is suitable for both the common screw and the locking screw, and screws can be selected according to operators' need.

The method of using the fixing device is as follows:

During the operation, the pelvic anterior approaches are adopted (supra-ilioinguinal or pararectus approach). Conventional incising skin, subcutaneous tissue, three layers of abdominal muscle; ligating of the inferior epigastric artery; exposing the spermatic cord (or round ligament of uterus), iliac vessels and the pubis; ligating corona mortis if found; then using a stripping ball made of wet gauze to separate the peritoneal and organs inside the pelvic cavity from the outside surface of iliopsoas; exposing the arcuate margin A5, further down the exposure of quadrilateral plate A4 and partial ischium A6.

Under direct vision, anatomical reduction is obtained as far as possible and then a iliopectineal plate B1 can be placed. Referring the medial anatomic structure of the iliopectineal margin A5, let the iliopectineal plate B1 match with the anatomic radian of the iliopectineal margin A5 and the upper part of quadrilateral surface A4, as well as make the posterior column arm B3 match with the anatomic radian of the iliac fossa A1.

With the upper ramus of the pubis bone A2 as the point of reference, the pubic plate B2 was inserted from the anterior and posterior part of the iliac vascular bundle, and the iliopectineal plate B1 is located at the medial surface of the iliopectineal margin A5 according to the anatomic radian of iliopectineal structure. The pubic plate B2 was matched with the radian of the medial surface of the superior pubic ramus A2. The step 22 at the second screw hole D2 of the pubic plate B2 is able to be matched with the groove 21 at the first screw hole D1 of the iliopectineal plate B1, then a short connecting screw can be inserted into the first screw hole D1 (the second screw hole D2) combining the two plates into a whole. One or two Kirschner wires are inserted into the temporary fixing holes 12 in the iliopectineal plate B1 or pubic plate B2.

To select the appropriate screw holes on the iliopectineal plate B1 and the pubic plate B2, two ordinary screws were inserted to make the steel plate adhere to the bone surface. The anterior column A11 and the acetabular quadrilateral area A4 were fixed too.

Select two suitable screw holes of the posterior column arm B3 and put a long locking screw into each hole to fix the posterior column A9. If there are a few gaps in the posterior column A9, a long lag screw can be inserted to further restore the fracture, after press firmly, and then insert a locking screw into the other screw hole.

For the existence of pubic longitudinal fractures, insert a screw into the third hole G of the pubic arm B4, fixing superior pubic ramus A2 perpendicularly to the fracture line; for the fracture of non bone longitudinal fracture, can remove the pubic arm B4 from the pubic plate B2.

In the remaining screw holes, the screws are inserted at the right place and the whole plate is firmly fixed to the anatomical structure.

Embodiment 2

Figure 4:
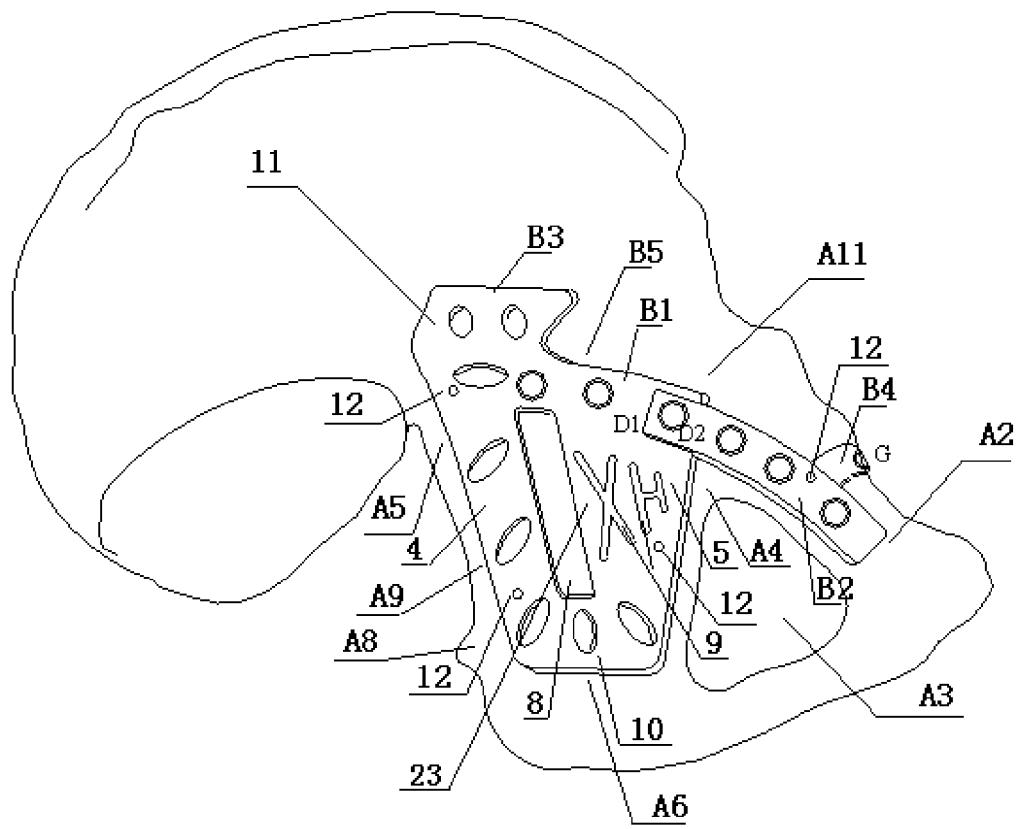
FIG. 4 is a schematic diagram of the embodiment 2 that a device for fixing the acetabular anterior/posterior column and quadrilateral plate fracture, which has been installed on the acetabulum.

As shown in FIGS. 3 and 4, fixing device of anterior/posterior column and quadrilateral plate fractures include: Trapezoidal plate B5 and pubic plate B2. Both two plates are concave-convex shaped plate structure with same thickness and made of medical titanium alloy.

The upper edge of the trapezoidal plate B5 is transversely designed with an iliopectineal plate B1. The structural design of the iliopectineal plate B1 and the first screw hole D1 in it are identical to the embodiment 1.

The other side of the trapezoidal plate B5 which is matched with the structure of posterior column A9 below the iliopectineal margin A5 is designed with the posterior column plate 4. The top of the posterior column plate 4 intersects the iliopectineal plate B1 and extends to the iliac fossa A1, extending out of the posterior column arm B3. The structural design and implementation of the arm B3 are identical to the embodiment 1.

The bottom of the posterior column plate 4 is transversely connected to one end of the sciatic plate 10, which forming the bottom margin of the trapezoidal plate B5. The sciatic plate 10 is curved to match with the sciatic A6 anatomic physiologic radian between the sciatic spine A8 and the obturator A3.

The posterior column plate 4 and sciatic plate 10 are designed with a plurality of oblique combination guide locking screws holes, and can be fixed by an ordinary screw or by a locking screw. The posterior column arm B3 is designed with a plurality of combining screw holes from the outside to the inside.

Along the edge of posterior column plate 4 and sciatic plate 10 is also designed with several temporary fixing hole of Kirschner wire 12, which can be set up at the top of the lateral posterior column plate 4, or the junction of posterior column plate 4 and sciatic plate 10, or at the top edge of sciatic plate 10.

The quadrilateral buttress plate 5 is also designed between the upper and the lower bottom edges of the trapezoidal plate B5. The quadrilateral buttress plate 5 includes: posterior column window 8 and acetabulum quadrilateral plate 9. The quadrilateral buttress plate 5 is a thin palisading structure, and is matched with the anatomic structure of the quadrilateral area A4. Through the posterior column window 8 and acetabulum quadrilateral plate 9, the whole posterior column A9 could be observed. During the operation, a stick or hook can be inserted into the back window 8 to assist the residual column A9 shift so as to better restore it and restore the anatomic structure of the posterior column A9 as much as possible. The interior palisading structure of the quadrilateral buttress plate 5 is designed with acetabulum quadrilateral plate 9, namely a X shaped and H shaped hole, which is also able to be inserted to assist reducing and observing the fracture of the acetabulum quadrilateral plate A4.

The structural design of the pubic plate B2 and its second screw D2 and the pubic arm B4 are identical to those of the embodiment 1.

Identical to the embodiment 1, the shape of the step 22 at the second screw hole D2 and the groove 21 of the first hole D1 are exactly matched. At this moment, the first screw hole D1 aligns with the second screw hole D2 properly. Then a short connecting screw is used to cross the second screw hole D2 and the first screw hole D1 to combine the trapezoidal plate B5 and the pubic plate B2 as a whole. The combination of the trapezoidal plate B5 and the pubic plate B2 does not move or rotate with each other, nor does it move or rotate on the anatomical site. The pubis plate B2 and the iliopectineal plate B1 are bent to match with the medial anatomic structure of the superior pubic ramus A2 and iliopectineal margin A5.

The shape of the trapezoidal plate B5 and pubic plate B2 are all match well with the anatomic structure of acetabular area A4, anterior column A11 and posterior column A9, especially the superior pubic ramus A2 and ilio-pectineal margin A5, so it is easier to operate without pre-bending.

With reference to the anatomic physiological radian between the iliopectineal margin A5 and the ischium A6, the trapezoidal plate B5 is positioned on the medial side of the acetabulum. It should be noted that the distance between the trapezoidal plate B5 and the posterior column A9 is no more than 5 mm. With reference to the anatomic physiological radian of the superior pubic ramus A2, the pubic plate B2 was positioned on the medial surface of the superior pubic ramus A2.

The posterior column plate 4 and the sciatic plate 10 of the trapezoidal plate B5 are placed from the medial side of acetabulum fixing the posterior column A9 and the ischium A6. According to the fracture need, the posterior column plate 4 or the sciatic plate 10 is fixed with at least one screw. The holes of posterior column plate 4 and sciatic plate 10 are oblique combined guide locking holes, which will guarantee the screws being unable to slip into the joint cavity and without repeat fluoroscopy.

The fixing device is used as follows:

Identical to the embodiment 1, during the operation, the anterior approach of the pelvis is used to expose the iliopectineal margin A5, and downward exposure of the acetabular quadrilateral area A4, as well as partial ischium A6.

Anatomical reduction is obtained under direct visualization, and then put trapezoidal plate B5. With the reference of iliopectineal margin A5, the iliopectineal plate B1 of trapezoidal plate B5 was matched with iliopectineal margin A5 and the posterior column plate 4 and quadrilateral buttress plate 5 was respectively matched with the anatomic structure of posterior column A9 and quadrilateral area A4. One or two Kirschner wires are placed into the Kirschner wire temporary fixing hole 12 on the trapezoidal plate B5 for temporary fixation.

The pubic plate B2 is inserted below the iliac neurovascular bundle from front to back. After the second screw hole D2 on the suprapubic plate B2 is aligned with the first screw hole D1 on the trapezoidal plate B5, a short connecting screw is fixed, and the trapezoidal plate B5 is connected with the B2 of the pubic plate. One or two Kirschner wires are inserted into the temporary fixing holes 12 in the trapezoidal plate B5 for temporary fixation.

To select the appropriate screw holes on the iliopectineal plate B1 or the pubic plate B2 or pubic arm B4, two ordinary screws were inserted to make the steel plate adhere to the bone surface. The anterior column A11 and the acetabular quadrilateral area A4 were fixed too. For the existence of pubic longitudinal fractures, a screw is inserted into the third screw hole G of the pubic arm B4 for fixing the superior pubic ramus A2 perpendicularly to the fracture line. The third screw hole G is a combination screw hole, into which the ordinary screw or the locking screw can be placed. As for the fracture with non bone longitudinal fracture, the pubic arm B4 can be removed from the pubic plate B2.

In the remaining screw holes, the screws are inserted at the right place and the whole plate is firmly fixed to the anatomical structure.

If the posterior column A9 and quadrilateral area A4 has been reduced well, we can choose suitable holes of the posterior column plate 4 or sciatic plate 10 for placement of an ordinary screw. Then the whole plate could be further matched with the bone surface of quadrilateral area A4, admitting the posterior column A9 and quadrilateral area A4 to be fixed well. If there is residual displacement, a rod or a pulling hook can be inserted into the posterior column window 8 or quadrilateral plate window 9 to assist gaining an anatomical reduction. Then one or two lag screws (or ordinary screws) are inserted into the appropriate screw holes of the posterior column plate 4 or the posterior columnear arm B3 for fixing the posterior column A9 and quadrilateral area A4.

In the remaining holes, select the appropriate place to insert the screws and secure the whole plate firmly.

Embodiment 3

Figure 5:
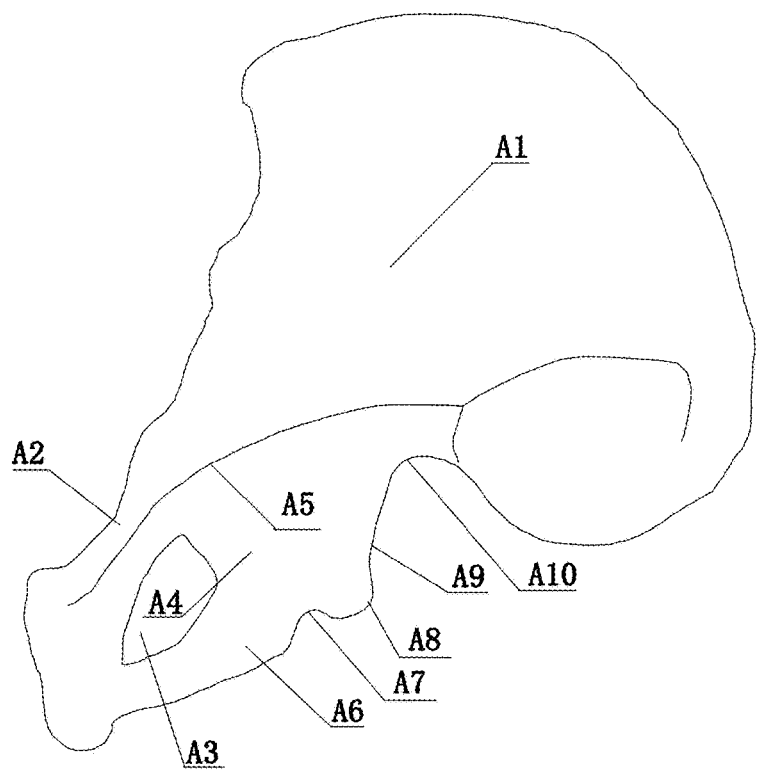
FIG. 5 is another sketch view of the acetabular and its adjacent anatomic structures.
Figure 6:
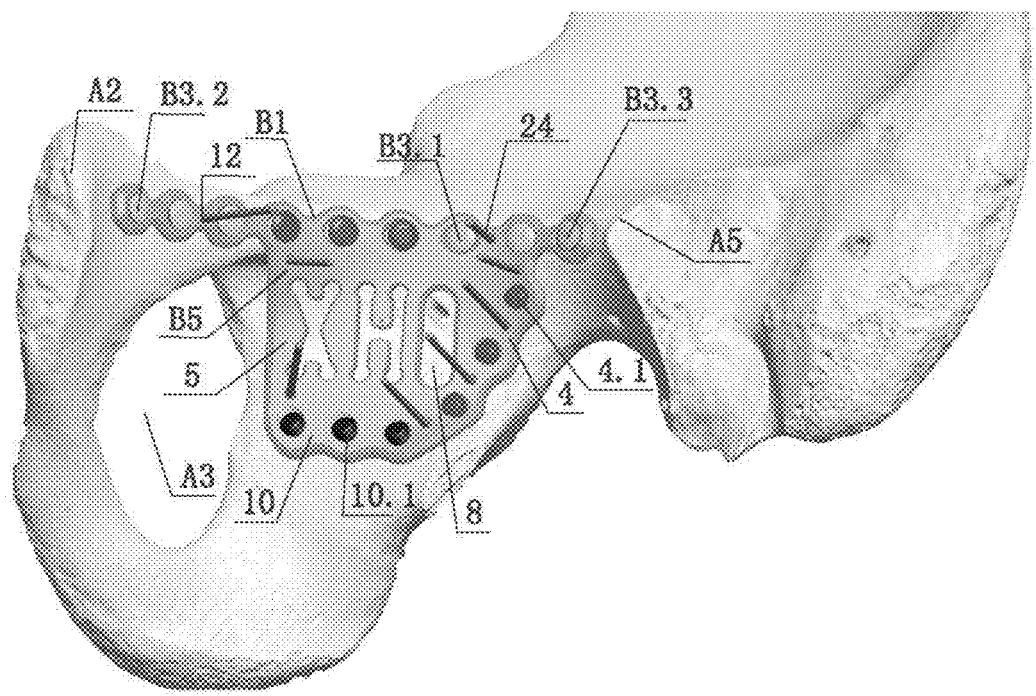
FIG. 6 is a schematic diagram of the embodiment 3 that an integrated device for fixing the acetabular anterior/posterior column and quadrilateral plate fracture in the lower posterior column scheme, which has been installed on the acetabulum.
Figure 7:
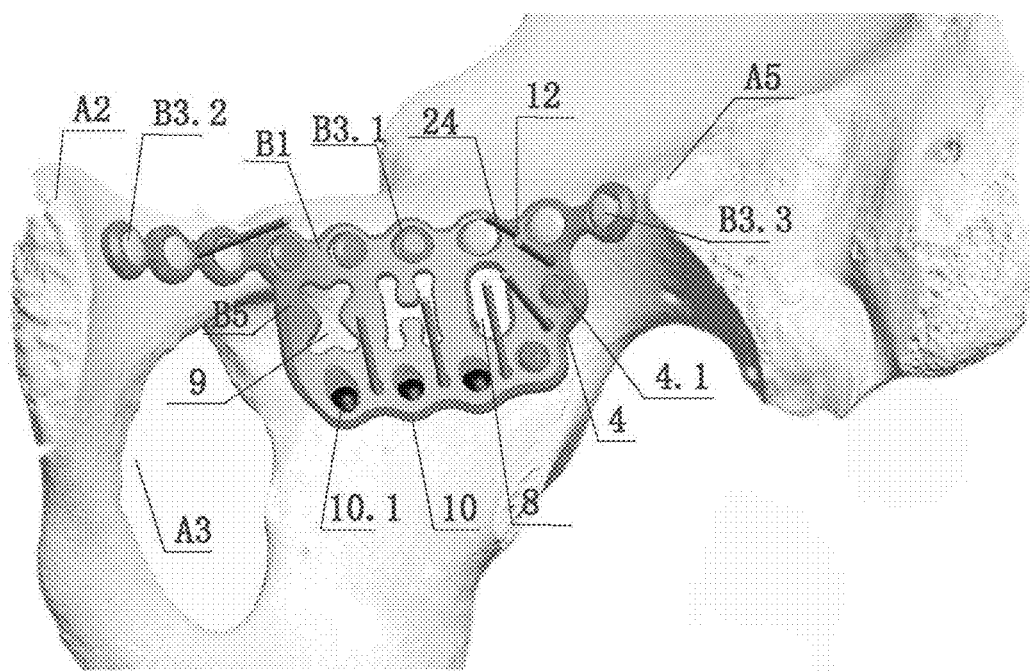
FIG. 7 is a schematic diagram of the case 3 that an integrated device for fixing the acetabular anterior/posterior column and quadrilateral plate fracture in the higher posterior column scheme, which has been installed on the acetabulum.

As shown in FIG. 5-7, the fixing device of anterior/posterior column and quadrilateral plate fractures is an integrated plate including a iliopectineal plate B1 and a trapezoidal plate B5. Both two is designed with concave convex plate structure in the same thickness and made of or medical stainless steel or titanium alloy.

The iliopectineal plate B1 is a strip transversely designed, which is bent to match with the medial anatomic structure of the iliopectineal margin. At the ends of iliopectineal plate B1 are respectively designed two ilium fixing hole B3.3 near the iliac fossa A1 and two pubis fixing holes B3.2 on the, and other five holes B3.1 is designed in the central part of iliopectineal plate B1. Both ilium fixing hole B3.3 and pubis fixing holes B3.2 are multiaxial locking screws with using locking screws. The middle holes B3.1 are designed using the ordinary screws. The iliopectineal plate B1 near the iliac fossa A1 and near the superior pubic ramus A2 are respectively designed one or two temporary fixing holes 12.

The trapezoidal plate B5 is transversely designed at the lower part of the iliopectneal plate B1, and is integrally bent to match with the inner anatomy of the upper half part of the quadrilateral area A4 and ischium A6. The upper part of the trapezoidal plate B5 is fitted with the anatomic structure of the bone surface from the greater sciatic notch A10 transversely to the obturator A3.

The upper part of the trapezoidal plate B5 is designed with a posterior column plate 4, a posterior column window 8 and a quadrilateral buttress plate 5. The posterior column plate 4 is located below the ilium fixing hole B3.3 and extends to the sciatic spine A8 along the bone surface of the posterior column A9. Three posterior column fixing holes 4.1 are designed on the posterior column plate 4, which are multi-axial locking screw holes and are matched with the locking screws. The posterior column window 8, the quadrilateral plate 5 and the acetabulum quadrilateral plate 9 are the same as the embodiment 1.

The bottom of the trapezoidal plate B5, the bottom of the column steel plate 3, the lower end of the posterior column window 8 and the lower part of the quadrilateral buttress plate 5 are designed with a sciatic plate 10. The sciatic plate 10 is bent to match the medial anatomic structure of the ischium A6. The sciatic plate 10 is designed with three sciatic fixing holes 10.1, which all are multiaxial locking screw holes. The bottom of the trapezoidal plate B5 is designed with two temporary fixing hole 12 for Kirschner pins, as well as another three temporary fixing holes 12 are designed at the lateral side of posterior column plate 4 and the lower side of sciatic plate 10.

When the iliopectineal plate B1 and trapezoidal plate B5 are placed on the acetabulum, the back of the whole plate was matched with the anatomic structure of the upper acetabular quadrilateral area A4, the medial side of the superior pubic ramus and the sciatic body. One end of the iliopectineal plate B1 is located at the medial side of the iliopectineal margin A5 and inferior side of the superior pubic ramus A2. Another end of the iliopectineal plate B1 is located at the extending line of the sciatic spine A8. The top of the posterior column plate 4 is located below the ilium fixing hole B3.3 and extends along the posterior column A9 bone toward the sciatic spine A8. The quadrilateral buttress plate 5 is located on the acetabular area A4. The superior part of the trapezoidal plate B5 is matched with the anatomic structure of the bone surface from the greater sciatic notch A10 transversely to the obturator A3.

As shown in FIG. 6, for acetabulum quadrilateral area A4 fracture involving lower posterior column, the sciatic plate 10 and trapezoidal plate B5 are placed just locating the bottom of sciatic spine A8 and top of lesser sciatic notch A7.

As shown in FIG. 7, for acetabulum quadrilateral area A4 fracture involving higher posterior column, the bottom of the sciatic plate 10 and trapezoidal plate B5 are placed at the position from the middle point between the greater sciatic notch A10 and sciatic spine A8 to the obturator A3 near the edge of quadrilateral surface A4.

The region of the ilio-pectineal margin A5 is well fixed from the medial lower direction through the ilium fixing hole B3.3 and the pubis fixing hole B3.2 on the trapezoidal plate B5. Posterior column plate 4 and sciatic plate 10 of the trapezoidal plate B5 are respectively designed with a posterior column fixing hole 4.1 and sciatic fixing hole 10.1, which can fix posterior column A9 and lower part of acetabular quadrilateral area A4 guaranteeing the recovery of lower acetabular fractures.

Embodiment 4

As shown in FIGS. 8-11, an iliopectineal plate B1 and a trapezoidal plate B5 are merged together, and they are roughly equal in thickness with a concave and convex plate-like structure, which are made of medical stainless or titanium alloy.

As shown in the embodiment 3, the iliopectineal plate B1 is arranged in strip-shape transversely, and the back side of it is bent to fit the anatomic structure of the medial surface below the iliopectineal line A5. Both ends of the iliopectineal plate B1 are respectively set with two ilium fixing holes B3.3 closed to the iliac fossa A1 and two pubis fixing holes A2 on the upper ramus of pubis B3.2. Both B3.2 and B3.3 are polyaxial locking screw holes, which are inserted by locking screws. Two Kirschner wire temporary fixing holes 12 are set at the end of the iliopectineal plate B1 closed to the iliac fossa A1. And the other end of the plate B1 is provided with a Kirschner wire temporary fixing hole 12 on the superior pubic ramus A2.

On the iliopectineal plate B1 and the trapezoidal plate B5, there are respectively provided with a extending arm C.1 and an arm fixing hole C.3, which are used to combine the two plates. The extending arm C.1 is set on the iliopectineal plate B1 or the trapezoidal plate B5, and the arm fixing and mounting hole C.3 is arranged on the trapezoidal plate B5 or the iliopectineal plate B1. Two plates nearby could combined firmly by the fixing arm C.1 and the arm fixing and mounting hole C.3.

On the extending arm C.1 of every group, the extending arm hole C.2 and extending arm fixing and mounting hole C.3 are combined holes, which are inserted with an ordinary screw or a connecting screw.

Figure 9:
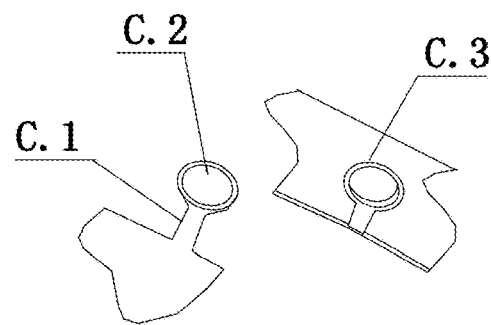
FIG. 9 is a diagram showing the installment of the extending fixation arm and the hole for fixing the arm.

For example, as shown in FIG. 9, in the middle of the top on the trapezoidal plate B5, there are four extending arms C.1. Respectively, at the bottom of the middle of the iliopectineal plate B1, there are four arm fixing and mounting holes C.3 in a row. They are combined to form four combined arms. The top of each extending arm C.1 is provided with an extending arm hole C.2.

The end of the extending arm C.1 is set a thin and step-like extending arm hole C.2. Every arm fixing and mounting hole C.3 is a sunken step-like hole. Every extending arm hole C.2 and the corresponding arm fixing hole C.3 shape with each other and after they are aligned, the screw is implanted to fix. The trapezoidal plate B5 and iliopectineal plate B1 are combined and matched with the anatomic structure of the anterior column and the iliopectineal line A5.

Figure 10:
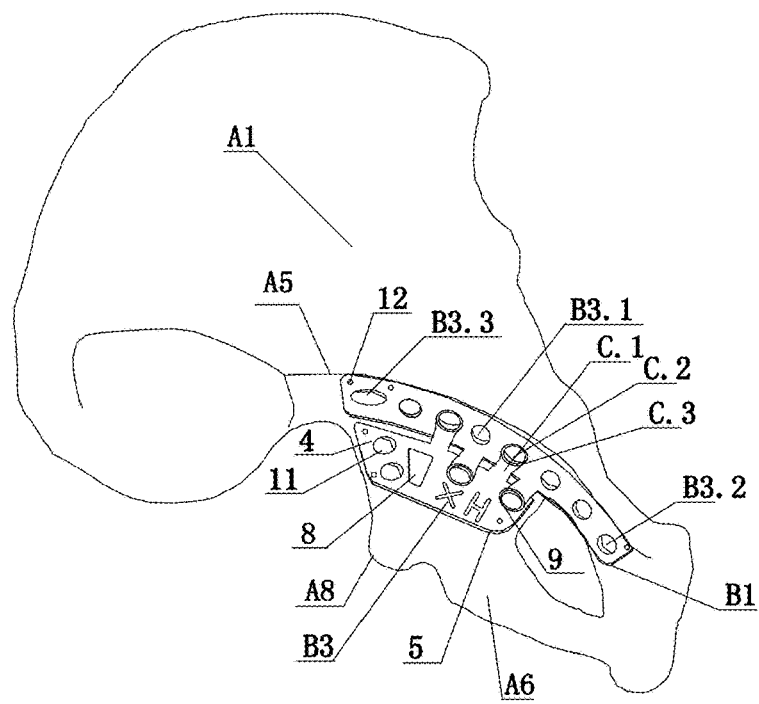
FIG. 10 is a schematic diagram of the embodiment 4 that an combined device for fixing the acetabular anterior/posterior column and quadrilateral plate fracture in the higher posterior column scheme, which has been installed on the acetabulum.

As shown in FIG. 10, the iliopectineal plate B1 and the trapezoidal plate B5 are connected by the intersection of the four extending arms C.1. The bottom of two adjacent extending arms C.1 is respectively arranged on the iliopectineal plate B1 and the trapezoidal plate B5. Accordingly, the bottom of each extending arm C.1 of the iliopectineal plate B1 is arranged with an iliopectineal line middle fixing hole B3.1. The quadrilateral area window 9 and the posterior column window 8 of the trapezoidal main board B5 are adjusted downward slightly.

Figure 11:
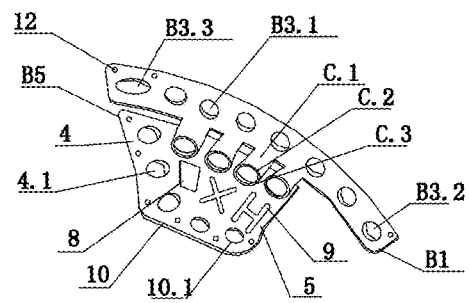
FIG. 11 is a schematic diagram of the embodiment 4 that an combined device for fixing the acetabular anterior/posterior column and quadrilateral plate fracture in the lower posterior column scheme.

As shown in FIG. 11, the iliopectineal plate B1 is provided with four extending arm C.1. The corresponding trapezoidal plate B5 is also provided with four arm fixing and mounting holes C.3. Accordingly, at the bottom of every extending arm C.1 of the iliopectineal plate B1 is arranged with an iliopectineal line middle fixing hole B3.1. The quadrilateral area window 9 and the posterior column window 8 of the trapezoidal main board B5 are adjusted downward slightly.

Figure 8:
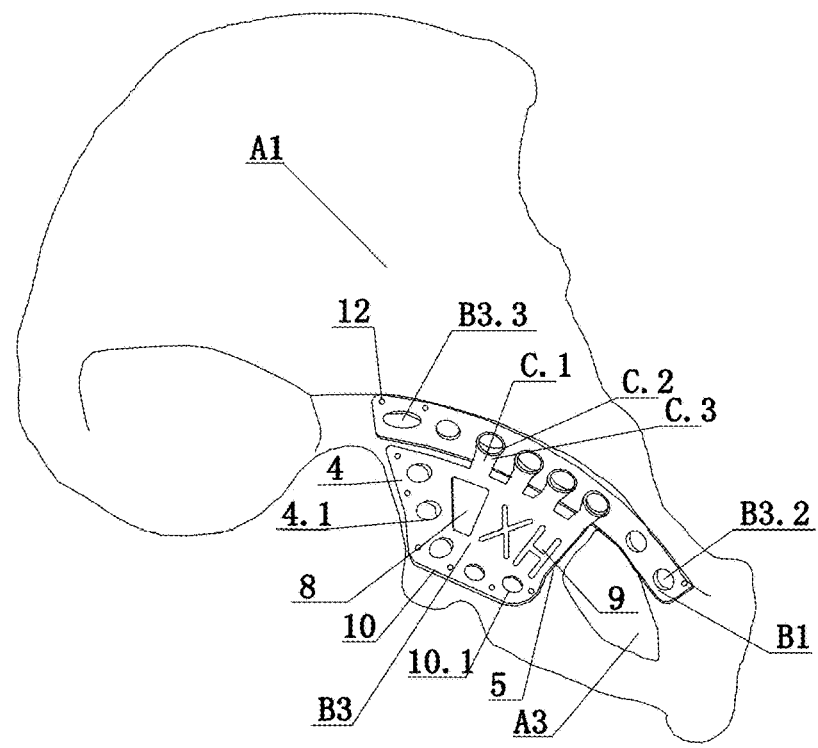
FIG. 8 is a schematic diagram of the embodiment 4 that an combined device for fixing the acetabular anterior/posterior column and quadrilateral plate fracture in the lower posterior column scheme, which has been installed on the acetabulum.

As shown in FIGS. 8 and 11, when the trapezoidal plate B5 is designed by a low position scheme, the trapezoidal plate B5 is transversely set in the lower part of B5. The trapezoidal plate B5 is bent with the medial anatomy of the upper part of the quadrilateral area A4 and the area above the sciatic A6. The upper part of the trapezoidal plate B5 is fitted with the anatomic structure of the bone surface from the greater sciatic notch A10 transversely to the obturator A3. The posterior column plate 4, the posterior column window 8 and the quadrilateral area buttress plate 5 are successively arranged on the upper half part of the trapezoidal plate B5.

When the iliopectineal plate B1 and trapezoid plate B5 are combined together, the whole back is matched with the anatomic structure of the upper part of acetabular quadrilateral area A4, the medial surface of the pubic ramus and the upper lateral part of the sciatic body. The end of the iliopectineal plate B1 covers the medial iliopectineal line A5 to the superior ramus of pubis A2, and the other end of the iliopectineal plate B1 ends at the extension line of the sciatic spine A8. The top of the posterior column plate 4 is located below the ilium fixing hole B3.3 and extends from the posterior column A9 to the sciatic spine A8, and the quadrilateral buttress plate 5 is located on the quadrilateral area A4 of the acetabulum. The sciatic plate 10 of trapezoidal plate B5 is located at the base of the spine A8 and the top of the lesser sciatic notch A7. The upper part of the trapezoidal plate B5 is fitted with the anatomic structure of the bone surface from the greater sciatic notch A10 transversely to the obturator foramen A3.

The upper part of the trapezoidal plate B5 is arranged with the posterior column plate 4, posterior column window 8 and quadrilateral buttress plate 5. The bottom end of the posterior column plate 4 is located at the middle of the greater sciatic A10 and the sciatic spine A8. The posterior column plate 4 is provided with two posterior column fixing holes 4.1. Both the two holes are multiaxial locking screw holes which inserted with the locking screws. The quadrilateral buttress plate 5 is provided with a quadrilateral area window 9. In the quadrilateral area window 9, the X and H shaped holes are used to observe the quadrilateral area A4 so as to reduce the fracture better and reconstruct the anatomic structure of the posterior column A9 as much as possible.

The sciatic plate 10 is transversely arranged at the bottom of the trapezoidal plate B5. The sciatic plate 10 is located below the posterior column plate 4, the posterior column window 8 and the quadrilateral buttress plate 5. The sciatic plate 10 of the trapezoidal plate B5 is located at the bottom of the spine A8 and the top of the lesser sciatic notch A7. The sciatic plate 10 is provided with three fixing sciatic holes 10.1. Every hole 10.1 is a multiaxial locking screw hole inserted with the locking screw.

The posterior column plate 4's later line and the sciatic plate 10's bottom line are respectively provided with three Kirschner wire temporary fixing holes 12.

As shown in FIG. 10, when the trapezoidal plate B5 is designed by a high position scheme, the trapezoidal plate B5 does not contain the sciatic plate 10. When the plate combined with the iliopectineal plate B1 and trapezoidal plate B5 was put on the medial surface of the iliopectineal line A5 and upper surface of the anterior column, the bottom of the posterior column plate 4 of the trapezoidal plate B5 is located at the middle point of line connecting greater sciatic notch A10 and sciatic spine A8. The bottom of the quadrilateral buttress plate 5 of the trapezoidal plate B5 is as high as the bottom of lateral line of obturator foramen closed to quadrilateral area.

The trapezoidal plate B5 using a high position scheme operates as follows:

Similarly, when surgeon adopts one anterior approach (supra-ilioinguinal approach or pararectus approach): conventional skin section, subcutaneous tissue section, three abdominal muscle layers section, ligation of the inferior epigastric artery, exposure of the spermatic cord and iliac vessels, pubis exposure, dealing with corona mortis, separating the peritoneum and the internal organs from the iliac psoas gently with the wet gauze and stripping ball, retraction of the iliac vessels inwardly or outwardly, exposure of the iliopectineal line A5, further exposure of acetabular quadrilateral area A4 and partial sciatic A6.

Step 1: Plate Placement and Connection

With the iliopectineal line A5, superior pubic ramus A2 and acetabular quadrilateral area A4 as the reference point, the iliopectineal plate B1 and the trapezoidal plate B5 are matched the iliopectineal line A5 and the quadrilateral area A4. The extending arm hole C.2 of the trapezoidal plate B5 and iliopectineal plate B1 get aligned to the extending arm fixing and mounting hole C.3 by implanting a combined screw to assemble the iliopectineal plate B1 and trapezoidal plate B5 as a whole;

Specifically, under direct vision, we do the best to reduce the fracture and then put in the trapezoidal plate B5. Taking the iliopectineal line A5 as the reference point, the anatomy radian of the iliopectineal plate B1 matches with the iliopectineal line A5. The posterior column plate 4 and the quadrilateral buttress plate 5 respectively match with the anatomic structure of the posterior column A9 and acetabular quadrilateral area A4. One or two Kirschner wires are implanted into the Kirschner wire fixing holes 12 to fix the trapezoidal plate B5 temporarily.

The iliopectineal plate B1 is inserted below the iliac neurovascular bundle. The extending arm hole C.2 of the extending arm C.1 on the trapezoidal plate and the extending arm fixing and mounting hole C.3 on the iliopectineal plate B1 get aligned and then insert a short combined screw to assemble the iliopectineal plate B1 and trapezoidal plate B5 together. The Kirschner wire is implanted into the temporary Kirschner wire fixing holes 12 on the iliopectineal plate B1 for temporary fixing.

Step 2: Temporary Fixation of Plate

The iliopectineal plate B1 and trapezoidal plate B5 are temporarily fixed by choosing the K-wire fixing holes to insert Kirschner wires in. The fracture reduction is observed through the quadrilateral area window 9, posterior column window 8.

Step 3: Fixation of the Iliopectineal Line A5.

At least one pubis fixing hole B3.2 and one ilium fixing hole B3.3 on the iliopectineal plate B1 should be implanted with a screw to fix and match the iliopectineal plate to the iliopectineal line A5.

Step 4: Fixation of Posterior Column A9.

If the fracture of the posterior column A9 and the quadrilateral area A4 were well reduced, we can choose a posterior column fixing hole 4.1 on the posterior column plate 4 or a sciatic fixing hole 10.1 on the sciatic plate 10 implanting a screw to make the posterior column plate 4 or the sciatic plate 10 attached to the bone surface of the acetabular quadrilateral area A4, and fix the posterior column A9 and acetabular quadrilateral area A4.

If the fracture of the posterior column A9 and the acetabular quadrilateral area A4 were not well reduced and remained micro-displacement, we can insert the ball-spike pusher or the lift hook into the quadrilateral area window 9 of quadrilateral buttress plate to reduce the fracture displacement well. Then at least one posterior column fixing hole 4.1 or at least one the sciatic fixing holes 10.1 should be implanted into a screw to fixed posterior column A9 and acetabular quadrilateral area A4.

Step 5: The Remaining Screws' Fixation

Select the appropriate screw hole to implant the screw to fix the iliopectineal plate B1 and the trapezoidal plate B5 tightly.

When the trapezoidal plate B5 of the high position scheme was chosen, the fixed device of the posterior column A9 was not set. Not fixing the low level acetabular fracture or the low level fracture of posterior column A9, one ilium fixing hole B3.3 of the trapezoidal plate B5 is inserted one screw to fix the iliopectineal line A5 well.

The operation method of the trapezoidal plate B5 using low position scheme is different from that of the above high position scheme. The differences are:

The posterior column A9 area of the trapezoidal plate B5 is also set with posterior column plate 4 and steel plate 10. In contrast, the trapezoidal plate B5 of low position scheme is designed also aim at the low position acetabular fracture, or the low position fracture of posterior column A9, not only at the high position fracture of the iliopectineal line A5.

By fixing the ilium fixing hole B3.2 and pubis fixing hole B3.3 of the trapezoidal plate B5, the iliopectineal line A5 was fixed well. The posterior column 4 and sciatic plate 10 of the trapezoidal plate B5, respectively, are set with posterior column fixing holes 4.1 and the sciatic fixing hole 10.1, which can respectively fix the posterior column A9 and the underside area of the acetabular quadrilateral area A4 to guarantee the acetabular low position fracture can be reduced.

As mentioned above, compared with traditional methods, the invention can fix the anterior column A11, the posterior column A9 and the acetabular quadrilateral area A4 at the same time with less complications after operation. It is mechanical matched well and easy to operate. Specifically:
1. Iliopectineal line A5:

The bone of iliopectineal line A5, which is located between the anterior column A11 and the posterior column A9, is very thick and can bear more force. A serious comminuted fracture does not happened at the iliopectineal line A5 usually. Therefore, the other area fracture fragments could fixed at the iliopectineal line A5 to get good stability.

In particularly, the iliopectineal plate B1, which is located below the medial surface of iliopectineal line A5 and attach to the bone surface well, could provide strong buttress power for iliopectineal line A5. But in the existing techniques (such as patent CN201831946U), the plate was located on the superior surface of iliopectineal line A5, which is not at the displacing direction of the quadrilateral plate fracture fragments. So these plates cannot provide good mechanical support. The invention is arranged on the inner side of the iliopectineal margin, which just contrary to the inward displacement of the acetabulum quadrilateral plate fracture fragment. So the displacement of the acetabulum quadrilateral plate fracture can be buttressed from the inside to the outside in a better biomechanical way.
2. Acetabulum quadrilateral plate A4:

Generally the displacement direction of acetabular quadrilateral area A4 fracture fragments is from outside to inside. The entire acetabulum quadrilateral plate A4 can be covered by the large trapezoidal plate B5 which comprises the posterior column plate 4, the sciatic plate 10 and the quadrilateral buttress plate 5. The trapezoidal plate locates on the medial surface of the quadrilateral plate A4, just buttress the quadrilateral area A4 from inside to outside. If there is a comminuted fracture of the acetabulum quadrilateral plate A4, whose fragments cannot be fixed one by one, the sciatic plate 10 can be used to reduce and buttress the fragments. In addition, the posterior column window 9 is set on the sciatic plate 10, through which a ball-spike pusher or pulling hook can be inserted to assist reducing acetabular posterior column A9 or quadrilateral plate A4 fracture, as well as the reduction of fracture can be observed.

For the prior art, such as patent CN201831946U, the quadrilateral buttress was designed vertically which can only contrary to part of the quadrilateral plate. However the device 5 of our design can cover the entire acetabulum quadrilateral plate A4.
3. For the anterior column A11: the displacement direction of most anterior column A11 fracture is from outside to inside, so placing the iliopectineal plate B1 and pubic plate B2 on the medial surface of the iliopectineal line A5 to obtain a fixation from inside to outside in the embodiments 1 and 2. Alternatively, just like the integrated iliopectineal plate B1 in the embodiments 3 and 4, the superior pubic ramus A2 is fixed by the pubis fixing hole B3.2 and the inner side of the iliopectineal line A5 is fixed by the ilium fixing hole B3.3 from the other side.
4. For the posterior column A9, not only a posterior column arm B3 is designed to fix the posterior column A9 in this invention, but also a posterior column plate 4. The screws are selectively inserted in different screw holes of the posterior column plate 4 for the fixations of the upper or lower fracture of the posterior column A9.

For extremely lower fractures of posterior column A9, the fractures cannot be fixed by the posterior column arm B3 or the posterior column plate 4, using sciatic plate 10 can obtain a good fixation. The displacement of the fracture of the posterior column A9 can be reduced by a ball-spike pusher or pulling hook through the posterior column window 8 within the quadrilateral buttress plate 5. The reduction is also could be checked through window 8. The screw holes on the posterior column plate 4 and sciatic plate 10 are all combined screw holes to prevent the screw from entering the joint cavity. An ordinary screw can be inserted to make the plate adhere to the bone surface, or the locking screw can also be inserted.
5. For superior pubic ramus A2: the pubic arm B4 on the pubic plate B2 which can be broken off and removed easily is especially suitable in the fixation of longitudinal fracture on superior pubic ramus A2. If the pubic bone fracture is a transverse fracture, the pubic arm B4 is not needed. It can be broken and removed directly. It provides a flexible and diverse fixation method for different types of pubic fractures.
6. The two plates mentioned in examples 1 and 2 are connected with the combined screws to reduce the operation time and avoid the fatal complications such as blood vessel and nerve injury. The existing technical patent CN201831946U provides the plate as an integral type which is not easy to place during the operation. Because the iliac artery and the iliac vein above the iliopectineal line A5, the entire plate is inserted below the iliac vessels and femoral nerve and placed above the iliopectineal line A5, which is difficult to perform.

The iliopectineal plate B1 and the pubic plate B2 were positioned along the iliopectineal line A5 and superior pubic ramus A2. The medial surface of the line from the iliopectineal line A5 to the upper ramus of pubis A2 is smooth. The iliopectineal plate B1 and the pubic plate B2 designed in the invention can be bent to match with the anatomic structure well, and can be attached to the inner part of the anterior column A11, the posterior column A9 and the acetabulum quadrilateral plate A4.

It's not necessary for separating inguinal ligament from the upper surface of superior pubic ramus A2. Iliac sham, pubic comb ligament and lacunae ligament are also not necessary to be separate. The iliopectineal plate B1 and pubic plate B2 could be placed at the iliopectineal line A5 and superior pubic ramus A2 easily by the pararectus approach or high ilioinguinal approach. Simultaneously, the plate we designed is combined with two parts: iliopectineal plate B1 and pubic plate B2. The pubic plate B2 with simple structure and short length can be easily inserted through the iliac vessels and the spermatic cord (round ligament of the uterus), attached to the superior pubic ramus A2, then combined with iliopectineal plate B1 by the connecting screw.

Therefore, the placement of the anterior/posterior column plate we designed could lead less surgical risk and postoperative potential complications. It could also reduce the operation time and avoid the possibility of the occurrence of inguinal hernia, vascular and nerve injury and fatal complications.

When adopt the methods of examples 3 and 4, the plate at the iliopectineal line A5 is designed as an iliopectineal plate B1 which is convenient to fit the bone surface of the lower edge of iliopectineal line A5, whose structure is uniform and stable. A variety of different fixation arm C.1 settings are used to endure forces in different directions from the iliopectineal line A5 for different fracture conditions. High or low two trapezoidal plate B5 are designed for high or low acetabular fractures.

The screw holes of the invention are designed as combined screw holes, which can be used as an ordinary screw or a locking screw. It is especially suitable for middle-aged and elderly patients with osteoporosis, preventing the plate from loosening and displacing, improving the quality of internal fixation and reducing the complication. Our invention can satisfactorily treat the comminuted fractures of the acetabular region, especially the iliopectineal line A5, the acetabulum quadrilateral plate A4 and the posterior column A9, which is difficult to anatomically restore. The use of the acetabular anterior column and the lower posterior column fracture fixation plate can achieve the triangle fixation of the iliopectineal line A5, acetabulum quadrilateral plate A4 and the posterior column A9 as a whole, and can enhance the quality of fracture reduction and internal fixation. The use of the invention is conducive to early postoperative exercise and hip function recovery. The treatment effect is good. The invention is a very innovative treatment of acetabular fractures, which is worth to be widely spread.

Other unspecified contents belong to the ordinary technology existing.

The invention claimed is:

1. A device for fixing acetabular fractures involving the anterior/posterior column and quadrilateral plate, comprising:
    an iliopectineal plate; and
    a pubic plate;
    wherein,
    the iliopectineal plate matches with a medial anatomic structure of an iliopectineal line, one end of the iliopectineal plate is designed with a first screw hole matching the iliopectineal line near a superior pubic ramus and the other end of the iliopectineal plate is designed with a posterior column arm matching the iliopectineal line near an iliac fossa, a groove is disposed at the first screw hole of the iliopectineal plate adjacent to the pubic plate, the posterior column arm laterally extends from the iliopectineal plate and matches with the anatomic structure of the iliopectineal line extending to the iliac fossa, the posterior column arm is disposed with at least one screw hole;
    the pubic plate is disposed transversely in an arcuate way and is bent to fit a medial anatomic structure of the superior pubic ramus, one end of the pubic plate is designed with a second screw hole that matches with the superior pubic ramus near a pubic symphysis and the other end of the pubic plate is designed with a pubic arm extending to an upper surface of a pecten pubis near a pubic tubercle, the second screw hole is thinned into a step at an adjacent end of an arcuate plate;
    each of the iliopectineal plate and the pubic plate is provided with at least one Kirschner wire temporary fixing hole, the groove of the first screw hole of the iliopectineal plate and the thinned step of the second screw hole of the pubic plate match with each other, screws are provided to cross the first screw hole and the second screw hole that are aligned; the iliopectineal plate and the pubic plate are combined into a whole, the whole matches with anatomical structures of inner sides of the superior pubic ramus, an acetabulum quadrilateral plate and a posterior column.

2. The device for fixing acetabular fractures involving the anterior/posterior column and quadrilateral plate as claimed in claim 1, wherein the pubic arm is provided with at least one combined screw, the posterior column arm is provided with at least two combined screw holes and fixed by long lag screws or long locking screws, the screw holes of the iliopectineal plate and the pubic plate are in a form of combined screw holes.

3. A method of using a device for fixing acetabular fractures involving the anterior/posterior column and quadrilateral plate, the method comprising:
    a) placing and connecting plates
    matching an iliopectineal plate and an pubic plate with an inner anatomic structure of an iliopectineal line, an acetabulum quadrilateral plate and a superior pubic ramus by taking the iliopectineal line and the superior pubic ramus as a reference point; and inserting a short connecting screw into a first screw hole of the iliopectineal plate and a second screw hole of the pubic plate to make the iliopectineal plate and the pubic plate integrate together after the first screw hole of the iliopectineal plate and the second screw hole of the pubic plate are aligned;
    b) temporarily fixing the plates
    choosing two or three Kirschner wire temporary fixing holes on the iliopectineal plate, the pubic plate and a posterior column arm and respectively inserting a kirschner wire into the Kirschner wire temporary fixing holes on the iliopectineal plate, the pubic plate and the posterior column arm; and temporarily fixing the iliopectineal plate, the pubic plate and the posterior column arm on an anatomical structure;
    c) fixing an anterior column and the acetabulum quadrilateral plate
    inserting a screw into the iliopectineal plate and the pubic plate respectively for attaching the plate to a bone surface and also for fixing an upper part of the anterior column and the acetabulum quadrilateral plate;
    d) fixing a posterior column
    selecting two screw holes of the posterior column arm to be inserted with a long locking screw to fix the posterior column; and firstly inserting a long lag screw to further reduce the fracture displacement when there is a small gap between the posterior column plate and the bone surface, and then inserting a locking screw;
    e) fixing other screws
    fixing the iliopectineal plate and the pubic plate firmly by screws; and when there is a longitudinal cleft fracture of a pubis, using a third screw hole (G hole) on an arm of a pubic arm to fix the superior pubic ramus in a way perpendicular to a fracture line; and when there is no longitudinal cleft fracture of the pubis, broking off the pubic arm from the pubic plate.

4. A device for fixing acetabular fractures involving the anterior/posterior column and quadrilateral plate, comprising:
- a trapezoidal plate; and
- a pubic plate;
- wherein,
- an upper part of the trapezoidal plate is a transversely arranged iliopectineal plate, the iliopectineal plate is capable of being bent to match an anatomic structure of a medial side of an iliopectineal line, one end of the iliopectineal plate is matched with the iliopectineal line near an superior pubic ramus where a first screw hole is provided, a transversely arranged groove is provided from the iliopectineal plate to an adjacent end of the first screw hole;
- the other end of the iliopectineal plate is provided with a longitudinally arranged posterior column plate, the posterior column plate constitutes one side of the trapezoidal plate, the posterior column plate is capable of being bent to fit an anatomic structure of a medial side of the posterior column, a top of the posterior column plate connects to one end of the iliopectineal plate and bends toward an iliac fossa to extend from a posterior column arm, the posterior column arm matches with anatomic structures of the iliac fossa and the iliopectineal line;
- a bottom of the posterior column plate is attached to a sciatic plate, the sciatic plate is transversely disposed in a lower part of the trapezoidal plate, the sciatic plate is capable of being bent to fit an anatomic structure of a medial side of an ischium;
- the posterior column arm, the posterior column plate and the sciatic plate are provided with at least one screw hole and at least one Kirschner wire temporary fixing hole;
- an area between the sciatic plate and the iliopectineal plate is a quadrilateral buttress plate with a thin palisade structure, the area matches with the anatomic structure of an acetabulum quadrilateral plate, a posterior column window and a quadrilateral plate window are designed on the quadrilateral buttress plate;
- the pubic plate is curved and is capable of being bent to match with an anatomic structure of the superior pubic ramus, a second screw hole is disposed on a place where an end of the pubic plate is matched with a superior pubic ramus near a pubic symphysis, a portion from the second screw hole to an adjacent end of the pubic plate is thinned to a step;
- a groove of the first screw hole on the iliopectineal plate is matched with the thinned step of the second screw hole on the pubic plate, a screw is inserted into the first screw hole and the second screw hole for fixing after the first screw hole and the second screw hole are aligned;
- the trapezoidal plate and the pubic plate are combined as a whole and the whole matches with the anatomical structures of the acetabulum quadrilateral plate and the medial surface of the pubic ramus and an ischum.

5. The device for fixing acetabular fractures involving the anterior/posterior column and quadrilateral plate as claimed in claim 4, wherein at least one combined screw hole is provided on the pubic arm, a vacancy area between the quadrilateral buttress plate and the posterior column plate is a posterior column window, the posterior column window is located on an upper front part of the posterior column, at least two combined screw holes are disposed on the posterior column arm and fixed with a long lag screw or a long locking screw, at least three combined screw holes are disposed on the posterior column plate and the sciatic plate, all the screw holes disposed in the iliopectineal plate and the pubic plate are combined holes.

6. A method of using a device for fixing acetabular fractures involving the anterior/posterior column and quadrilateral plate, the method comprising:
- a) placing and connecting plates
- matching a trapezoidal plate and a pubic plate with an anatomical surface of an iliopectineal line and an acetabulum quadrilateral plate by taking the iliopectineal line, a superior pubic ramus and the acetabulum quadrilateral plate as a reference point; and inserting a short connecting screw into a first screw hole of the trapezoidal plate and a second screw hole of the pubic plate to make the trapezoidal plate and the pubic plate connected as a whole after the first screw hole of the trapezoidal plate and the second screw hole of the pubic plates are aligned;
- b) temporarily fixing the plates
- selecting two or three Kirschner wire temporary fixing holes to temporarily fix the trapezoidal plate and the pubic plate on an anatomical structure; and applying a fluoroscopy to observe a reduction of the fracture;
- c) fixing an anterior column
- inserting a screw into an iliopectineal plate and the pubic plate respectively for fixing the iliopectineal plate and the pubic plate on the anterior column;
- d) fixing the posterior column
- when the posterior column and the acetabulum quadrilateral plate have a good restoration, selecting one screw hole of a posterior column plate or a sciatic plate to be inserted with a screw for attaching the posterior column plate or the sciatic plate to a bone surface of the acetabulum quadrilateral plate and also fixing the posterior column and the acetabulum quadrilateral plate;
- when the posterior column and the acetabulum quadrilateral plate do not have a good restoration but have some micro displacement, applying an anatomical reduction on the micro displacement; then inserting a screw into at least one the screw hole of the posterior column plate or the posterior column to fix the posterior column and the acetabulum quadrilateral plate;
- e) fixing other screws
- fixing the trapezoidal plate and the pubic plate firmly by screws.

7. A device for fixing acetabular fractures involving the anterior/posterior column and quadrilateral plate, comprising:
- a strip-like iliopectineal plate; and
- a trapezoidal plate;
- wherein,
- the iliopectineal plate is set as a transverse strip and a back side of the iliopectineal plate is bent to fit an anatomic structure of an iliopectineal line;
- both ends of the iliopectineal plate are respectively provided with at least one ilium fixing hole and at least one pubis fixing hole, at least one iliopectineal line fixing hole is provided in a middle of the iliopectineal plate, the ilium fixing hole is set near an iliac fossa, the pubis fixing hole is configured to be set on a superior pubic ramus;
- the trapezoidal plate is transversely disposed on a lower part of the iliopectineal plate and is bent to match with an inner side anatomic structure of an upper part of an ischium and an upper part of an acetabulum quadrilateral plate, an upper part of the trapezoidal plate is matched with a bone surface anatomic structure from a greater sciatic notch to an obturator foramen transversely, a posterior column plate, a posterior column window and a quadrilateral buttress plate are disposed on the upper part of the trapezoidal plate in turn, a top of the posterior column plate is located below the ilium fixing hole and extends toward an ischial spine along a bone surface of a posterior column, the quadrilateral buttress plate is located on the acetabulum quadrilateral plate;

at least one posterior column fixing hole is provided on the posterior column plate, a quadrilateral plate window is provided on the quadrilateral buttress plate;

a sciatic plate is also arranged transversely at a bottom of the trapezoidal plate, the sciatic plate is located at a bottom of the posterior column plate and is below the posterior column window and the quadrilateral buttress plate, the sciatic plate is curved to fit the anatomic structure of the inside of the ischium, the sciatic plate is provided with an ischial fixing hole;

when the iliopectineal plate and the trapezoidal plate are attached to an inner surface of the iliopectineal line and an upper surface of the posterior column or an anterior column, a bottom of the sciatic plate of the trapezoidal plate is located at a bottom of the ischial spine and a top of a lesser sciatic notch, alternatively, the bottom of the sciatic plate of the trapezoidal plate is disposed at a position from a middle of the greater sciatic notch and the ischial spine to a bottom of the obturator foramen near the acetabulum quadrilateral plate.

8. The device for fixing acetabular fractures involving the anterior/posterior column and quadrilateral plate as claimed in claim 7, wherein the pubis fixing hole and the ilium fixing hole on the iliopectineal plate are universal locking screw holes which are inserted with locking screws, the trapezoidal plate is provided with at least two posterior column fixing holes and each posterior column fixing hole is a universal locking screw hole which is inserted with a locking screw, the sciatic plate is provided with at least two sciatic fixing holes and each sciatic fixing holes is a universal locking screw which is inserted with a locking screw, at least one Kirschner wire temporary fixing hole is arranged at each end of the iliopectineal plate, at least one Kirschner wire temporary fixing hole is provided on the bottom and a top of the trapezoidal plate.

9. A device for fixing acetabular fractures involving the anterior/posterior column and quadrilateral plate, comprising:

a strip-like iliopectineal plate; and
a trapezoidal plate combined with the strip-like iliopectineal plate as a whole;
wherein,
the iliopectineal plate is arranged stripe-like in a transverse direction and is curved to fit an anatomy of an inner side of an iliopectineal line, both ends of the iliopectineal plate are provided with at least one ilium fixing hole and at least one pubis fixing hole, the ilium fixing hole is near a fossa iliaca, the pubis fixing hole is located on a superior pubic ramus;

at least three fixing arms are provided between a top middle of the trapezoidal plate and a bottom middle of the iliopectineal plate, a bottom of each fixing arm is set at a top of the trapezoidal plate or a bottom of the iliopectineal plate, a top of each fixing arm is provided with an arm fixing hole, the bottom of the iliopectineal plate or the top of the trapezoidal plate which is not provided with the fixing arms is provided with an arm fixing and mounting hole;

a distal end of each fixing arm is provided with a thin step-like fixing arm hole, each arm fixing and mounting hole is a round hole recessed down into two steps, each fixing arm hole and a corresponding arm fixing and mounting hole are matched with each other, the fixing arm hole and the corresponding arm fixing and mounting hole are inserted by a screw to combine the trapezoidal plate and iliopectineal plate as a whole, the whole matches with the anatomic structure of the anterior column and the iliopectineal line;

the trapezoidal plate is arranged transversely in a lower part of the iliopectineal plate and curved with an anatomic structure of the ischium and an upper half of the acetabulum quadrilateral plate, an upper part of the trapezoidal plate is matched with the anatomic structure of a greater sciatic notch transverse to an obturator foramen, and a posterior column plate, a posterior column window and a quadrilateral buttress plate are disposed on the upper part of the trapezoidal plate in turn, when the iliopectineal plate and the trapezoidal plate are integrated, a top of the posterior column plate is located below the ilium fixing hole and extends along a posterior column to an ischial spine, the quadrilateral buttress plate is located on the acetabulum quadrilateral plate;

the posterior column plate is provided with at least one posterior column fixing hole, an quadrilateral plate window is disposed on the acetabular quadrilateral buttress plate;

a transverse part is set on a lower part of the trapezoidal plate which is integrally bent to match with an upper part of the ischium and an inner upper part of the acetabulum quadrilateral plate and also match with a bone surface anatomic structure from the greater sciatic notch to the obturator foramen.

10. The device for fixing acetabular fractures involving the anterior/posterior column and quadrilateral plate as claimed in claim 9, wherein the posterior column plate, the posterior column window and the acetabular quadrilateral buttress plate are disposed on the trapezoidal plate in turn, at least one posterior column fixing hole is provided on the posterior column plate, the quadrilateral plate window is provided on the acetabular quadrilateral buttress plate, when the iliopectineal plate and the trapezoidal plate are integrally attached to an inner side of the iliopectineal line and an upper surface of the anterior column, the top of the posterior column plate locates below the ilium fixing hole and extends to the ischial spine along the posterior column, and a bottom of the posterior column plate is located in a middle part from the greater sciatic notch to the ischial spine, the acetabular quadrilateral buttress plate is located on the upper part of the acetabulum quadrilateral plate, a bottom of the acetabular quadrilateral buttress plate has an equal height with an outer bottom of the obturator foramen near the acetabulum quadrilateral plate.

11. The device for fixing acetabular fractures involving the anterior/posterior column and quadrilateral plate as claimed in claim 9, wherein the posterior column plate, the posterior column plate window and the acetabular quadrilateral buttress plate are disposed on the upper part of the trapezoidal plate in turn, the sciatic plate is arranged on a bottom of the trapezoidal plate, the posterior column plate is provided with at least one posterior column fixing hole, the quadrilateral plate window is provided on the acetabular quadrilateral buttress plate, the sciatic plate is provided with at least one ischium fixing hole, when the iliopectineal plate and the trapezoidal plate are integrally attached to an upper surface of the iliopectineal line and the upper surface of the anterior column, the top of the posterior column is located below the ilium fixing hole and extends to the ischial spine along the posterior column, and the sciatic plate is located transversely at a bottom of the ischial spine and at a top of a lesser sciatic notch, the acetabular quadrilateral buttress plate is located on the upper part of the acetabulum quadrilateral plate, a bottom of the acetabular quadrilateral buttress plate has an equal height with a bottom of an outer edge of the obturator foramen near the acetabulum quadrilateral plate.

12. The device for fixing acetabular fractures involving the anterior/posterior column and quadrilateral plate as claimed in claim 9, wherein all the arm fixing hole and the arm fixing and mounting hole are combined screw holes, which could be inserted with ordinary screws or combined screws, the pubis fixing hole and the ilium fixing hole on the iliopectineal plate are universal locking screw holes inserted with locking screws, the trapezoidal plate is provided with at least two posterior column fixing holes, each posterior column fixing hole is a universal locking screw hole inserted with the locking screw, the sciatic plate is provided with at least two sciatic fixing holes, each sciatic fixing hole is a universal locking screw hole which is inserted by a locking screw, each end of the iliopectineal plate is provided with at least one Kirschner wire temporary fixing hole, at least one Kirschner wire temporary fixing hole is arranged at a bottom and the top of the trapezoidal plate.

13. A method of using a device for fixing acetabular fractures involving the anterior/posterior column and quadrilateral plate, the method comprising:
a) placing and connecting plates
matching an iliopectineal plate and a trapezoidal plate with an anatomic structure of an iliopectineal line and an acetabulum quadrilateral plate by taking the iliopectineal line, a superior pubis ramus and the acetabulum quadrilateral plate as reference points; and inserting a connection screw into every arm fixing hole and every corresponding arm fixing and mounting hole on the trapezoidal plate and the iliopectineal plate to make the iliopectineal plate and the trapezoidal plate connected as a whole after the arm fixing hole and the arm fixing and mounting hole are aligned;
b) temporarily fixing the plates
selecting one or two Kirschner wire temporary fixing holes of the iliopectineal plate and the trapezoidal plate respectively and temporarily fixing the iliopectineal plate and the trapezoidal plate on an anatomic structure; and observing a reduction of the fracture through a quadrilateral plate window and a posterior column window;
c) fixing the iliopectineal line
inserting a screw into at least one pubis fixing hole and at least one ilium fixing hole on the iliopectineal plate respectively for fixing the iliopectineal plate on the iliopectineal line;
d) fixing the posterior column
when the posterior column and the acetabulum quadrilateral plate are restored well, one posterior column fixing hole on a posterior column plate or one sciatic fixing hole on a sciatic plate is inserted with one screw to make the posterior column plate or the sciatic plate be attached to the bone surface of the acetabular quadrilateral plate and fix the posterior column and the acetabulum quadrilateral plate;
when the posterior column and the acetabulum quadrilateral plate do not have a good restoration but have some micro displacement,
applying an anatomical reduction on the micro displacement; then inserting a screw into at least one posterior column fixing hole or at least one sciatic fixing hole to fix the posterior column and the acetabulam quadrilateral plate;
e) inserting the remaining screws
fixing the iliopectineal plate and the trapezoidal plate firmly by screws.

* * * * *